United States Patent
Mariani et al.

(10) Patent No.: US 11,890,104 B2
(45) Date of Patent: Feb. 6, 2024

(54) SYSTEMS AND METHODS FOR DETERMINING PARTURITION ONSET IN ANIMALS

(71) Applicant: MARS, INCORPORATED, McLean, VA (US)

(72) Inventors: Claire Mariani, Aimargues (FR); Sylvie Chastant-Maillard, Toulouse (FR); Hanna Mila, Toulouse (FR); Fanny Aguer, Anglet (FR); Aurélien Grellet, Toulouse (FR); Achraf Adib-Lesaux, Aimargues (FR)

(73) Assignee: MARS, INCORPORATED, McLean, VA (US)

( * ) Notice: Subject to any disclaimer, the term of this patent is extended or adjusted under 35 U.S.C. 154(b) by 437 days.

(21) Appl. No.: 17/252,635

(22) PCT Filed: Jun. 21, 2019

(86) PCT No.: PCT/US2019/038522
§ 371 (c)(1),
(2) Date: Dec. 15, 2020

(87) PCT Pub. No.: WO2019/246549
PCT Pub. Date: Dec. 26, 2019

(65) Prior Publication Data
US 2021/0267534 A1 Sep. 2, 2021

Related U.S. Application Data

(60) Provisional application No. 62/688,193, filed on Jun. 21, 2018.

(51) Int. Cl.
*A61B 5/00* (2006.01)
*G16H 50/20* (2018.01)
*A61B 5/01* (2006.01)

(52) U.S. Cl.
CPC ............ *A61B 5/4343* (2013.01); *A61B 5/01* (2013.01); *A61B 5/686* (2013.01); *G16H 50/20* (2018.01); *A61B 2503/40* (2013.01)

(58) Field of Classification Search
CPC ........ A61B 2010/0029; A61B 10/0012; A61B 5/4343; A61B 5/01; A61B 2503/40; A61B 5/6875; A61D 17/008; G01K 1/024
See application file for complete search history.

(56) References Cited

U.S. PATENT DOCUMENTS

2009/0312667 A1* 12/2009 Utsunomiya ........ A61D 17/008
600/549
2010/0030036 A1* 2/2010 Mottram ............... A61B 5/6822
119/858

FOREIGN PATENT DOCUMENTS

KR 102219300 B1 * 2/2021 ............... A61B 5/00

OTHER PUBLICATIONS

Michel et al., Prediction of Parturition Date in the Bitch and Queen, Reprod Dom Anim 46, 926-932 (Oct. 2011).
(Continued)

*Primary Examiner* — Eric F Winakur
*Assistant Examiner* — Elina Sohyun Ahn
(74) *Attorney, Agent, or Firm* — Baker Botts L.L.P.

(57) ABSTRACT

Systems and methods for determining timing of parturition onset in non-human animals are provided. Specifically, a software application platform which provides a user with the ability to receive customized information relating to an animal's estimated parturition onset as displayed on a user interface. A user can input data, for example, one or more animal specific biomarkers, and subsequently receive identification of a predicted parturition onset timing and customized recommendations and/or intervention steps for the specific animal.

14 Claims, 6 Drawing Sheets

(56) References Cited

OTHER PUBLICATIONS

Kim et al., Parturition prediction and timing of canine pregnancy, Theriogenology, vol. 68, No. 8, Oct. 4, 2007, pp. 1177-1182.
Saint-Dizier et al., Methods and on-farm devices to predict calving time in cattle, Veterinary Journal, vol. 205, No. 3, Sep. 1, 2015, pp. 349-356.
International Search Report dated Aug. 9, 2019 for application No. PCT/US2019/038522, 3 pages.

* cited by examiner

SYSTEMS AND METHODS FOR DETERMINING PARTURITION ONSET IN ANIMALS

CROSS-REFERENCE TO RELATED APPLICATIONS

The present application claims the benefit of priority to U.S. Provisional Application Ser. No. 62/688,193, filed on Jun. 21, 2018, the contents of which is hereby incorporated by reference herein in its entirety.

1. FIELD OF THE INVENTION

The present disclosure generally relates to systems and methods for determining parturition onset in animals. More specifically, the present disclosure relates to systems and methods that enable a user, such as a veterinarian and/or breeder to evaluate and/or monitor one or more biomarkers of an animal to determine an estimated onset of parturition.

2. BACKGROUND

The timing of parturition in animals is used for both clinical and research purposes. For example, information regarding the approximate parturition date can be essential for the optimal management of pregnancy and for pregnancy monitoring of animals. The timing of parturition can involve several parameters and therefore parturition onset can be difficult to accurately determine. In the case of dogs, one parameter indicating impending parturition is a marked drop in body temperature approximately 24 hours prior to whelping. Body temperature can be measured, for example, through rectal or vaginal temperature. Another parameter in dogs which can indicate impending parturition is progesterone levels, for example, progesterone levels less than 2.7 ng/mL can indicate impending parturition in approximately 48 hours. The predicative value of body temperature variation to detect the onset of parturition, the factors influencing body temperature before parturition, and the threshold of body temperature variation to determine parturition onset has not been determined. Further, the predictive value of body temperature in association with other methods of parturition prediction parameters, such as, for example, progesterone levels has also not been evaluated.

Thus, there remains a need for systems and methods for accurate and reliable determination of parturition onset in animals in relation to one or more parturition prediction parameters. Accurate determination of parturition timing can be beneficial, for example, in organizing a maternity environment, in monitoring the animal accurately, and in organizing collaboration between veterinary surgeons and owners at the time of parturition. Further, accurate determination of parturition timing can aid in the detection of prolonged pregnancies and in the planning and performance of a caesarian section in safer conditions, for example, in the instance of high-risk pregnancies.

3. SUMMARY OF THE INVENTION

The present disclosure generally relates to systems and methods for determining parturition onset in animals. More specifically, the present disclosure relates to systems and methods that enable a user, such as a veterinarian and/or breeder to evaluate and/or monitor one or more biomarkers of an animal to determine an estimated onset of parturition.

In certain non-limiting embodiments, a method performed by a server for determining timing of parturition onset in non-human animals is provided. The method can include receiving, at the server, one or more first biomarkers relating to a first animal; determining, at the server, an estimated timing of parturition onset for the first animal based on the one or more first biomarkers; providing a customized recommendation based on the estimated timing of parturition onset; and transmitting, from the server, at least one of the customized recommendation or the estimated timing of parturition onset to a user computer.

In certain non-limiting embodiments, the method can further include comparing, at the server, the one or more first biomarkers relating to the first animal to at least one predetermined reference biomarker stored in a reference database. In certain non-limiting embodiments, the at least one predetermined reference biomarker can include a threshold value of the one or more first biomarkers. In certain non-limiting embodiments, the method can further include determining at least one of the estimated timing of parturition onset or the customized recommendation based on the threshold value of the one or more first biomarkers.

In certain non-limiting embodiments, the at least one predetermined reference biomarker can be based on the one or more first biomarkers received by the server for a second animal.

In certain non-limiting embodiments, the method can further include storing the received one or more first biomarkers relating to the first animal in the reference database. In certain non-limiting embodiments, the at least one predetermined reference biomarker can be based on the one or more first biomarkers relating to the first animal stored in the reference database.

In certain non-limiting embodiments, the method can further include receiving, at the server, at least one of a second or third biomarker, in which the first biomarker, the second biomarker, and the third biomarker can be different. In certain non-limiting embodiments, the method can further include determining, at the server, the estimated timing of parturition onset of the first animal based on the one or more first biomarkers and at least one of the second biomarker or the third biomarker.

In certain non-limiting embodiments, the one or more first biomarkers of the first animal can include at least one of a body temperature of the first animal or serum progesterone concentration of the first animal.

In certain non-limiting embodiments, the customized recommendation can include an intervention step requesting at least one additional biomarker for the first animal.

In certain non-limiting embodiments, the method can further include receiving, at the server, the at least one additional biomarker for the first animal in response to the intervention step. In certain non-limiting embodiments, the method can further include determining, at the server, the estimated timing of parturition onset for the first animal based on the additional biomarker.

In certain non-limiting embodiments, the one or more first biomarkers can be received from the user computer.

In certain non-limiting embodiments, the one or more first biomarkers can be received from a microchip implanted in the first animal.

In certain non-limiting embodiments, the server can be accessed using a global portal.

In certain non-limiting embodiments, a method performed by a user computer is provided. The method can include transmitting, from the user computer to a server, one or more first biomarkers relating to a first animal; receiving, at the user computer, at least one of a customized recommendation or an estimated timing of parturition onset for the first animal based on the transmitted one or more first biomarkers relating to the first animal; and displaying at least one of the customized recommendation or the estimated timing of parturition onset for the first animal on a graphic user interface of the user computer.

In certain non-limiting embodiments, the method can further include prompting a user to enter the one or more first biomarkers relating to the first animal. In certain non-limiting embodiments, the one or more first biomarkers can be received from an input by the user. Alternatively, in certain non-limiting embodiments, the one or more first biomarkers can be received from a microchip implanted in the first animal.

In certain non-limiting embodiments, the user can perform an intervention step in response to at least one of the customized recommendation or the estimated timing or parturition onset for the first animal.

In certain non-limiting embodiments, the method can further include transmitting, from the user computer to the server, at least one of a second or third biomarker, in which the first, the second, and the third biomarker can be different. In certain non-limiting embodiments, the method can further include receiving, at the user computer, at least one of the customized recommendation or the estimated timing of parturition onset based on the transmitted one or more first biomarkers and at least one of the second biomarker or third biomarker.

In certain non-limiting embodiments, the one or more first biomarkers of the first animal can include at least one of a body temperature of the first animal or serum progesterone concentration of the first animal.

In certain non-limiting embodiments, the receiving of the at least one customized recommendation can include an intervention step requesting at least one additional biomarker for the first animal.

In certain non-limiting embodiments, the method can further include transmitting, from the user computer to the server, the at least one additional biomarker for the first animal. In certain non-limiting embodiments, the method can further include receiving, at the user computer, the estimated timing of parturition onset of the first animal based on the additional biomarker.

In certain non-limiting embodiments, a server for determining timing of parturition onset in non-human animals is provided. The server can include a processor and a memory. The memory can store instructions that, when executed, cause the server to: receive one or more first biomarkers relating to a first animal; determine an estimated timing of parturition onset for the first animal based on the one or more first biomarkers; provide a customized recommendation based on the estimated timing of parturition onset; and transmit, from the server, at least one of the customized recommendation and the estimated timing of parturition onset to a user computer.

In certain non-limiting embodiments, the instructions stored by the memory, when executed by the processor, can further cause the server to: compare, at the server, the one or more first biomarkers relating to the first animal to at least one predetermined reference biomarker stored in a reference database, wherein the at least one predetermined reference biomarker comprises a threshold value of the one or more first biomarkers; and determine at least one of the estimated timing of parturition onset or the customized recommendation based on the threshold value of the one or more first biomarkers.

4. BRIEF DESCRIPTION OF THE DRAWINGS

DETAILED DESCRIPTION

Figure 1:
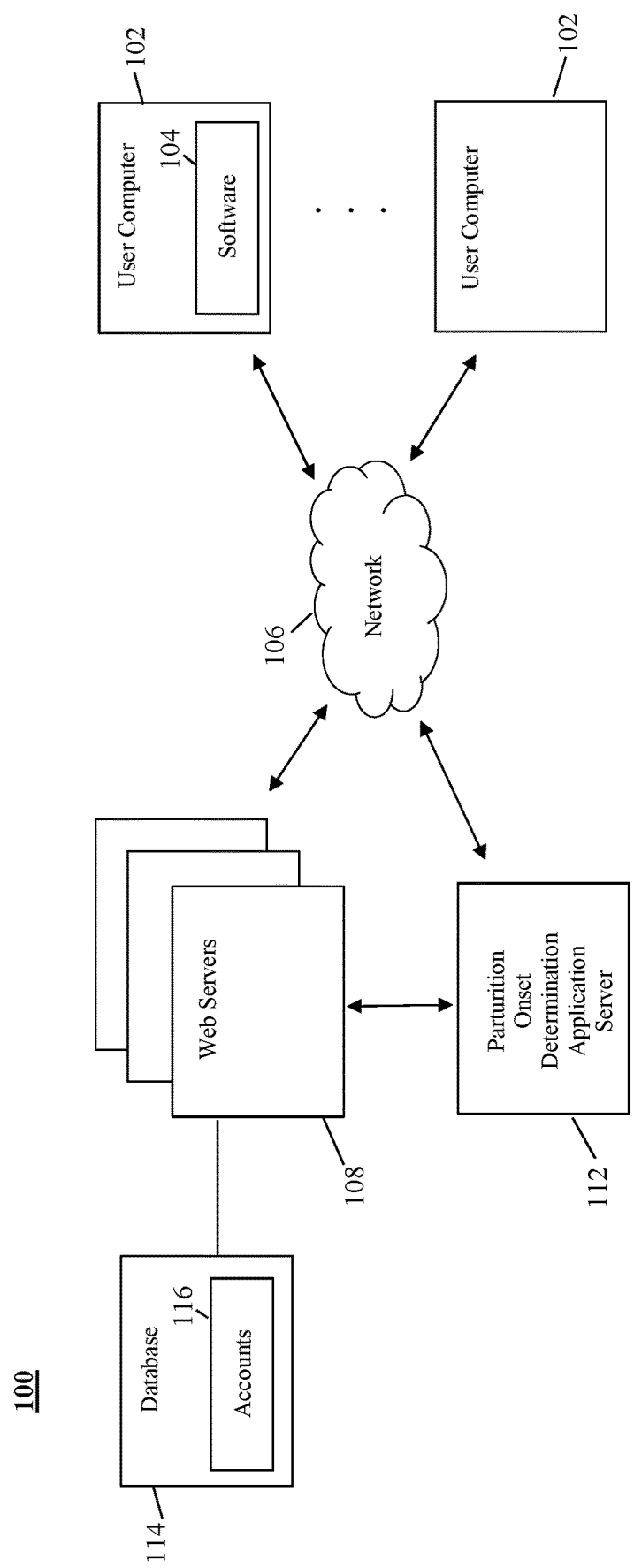
FIG. 1 illustrates a computer system configured to determine the parturition onset in accordance with certain non-limiting embodiments.

In certain non-limiting embodiments, the present disclosure generally relates to systems and methods for determining parturition onset in animals. More specifically, the present disclosure relates to systems and methods that allow a user, such as a veterinarian and/or breeder, to determine an estimated onset of parturition of an animal based on one or more biomarkers.

For clarity and not by way of limitation, this detailed description is divided into the following sub-portions:

5.1. Definitions;

5.2. Systems and methods for determining parturition onset in animals; and 5.3 Methods of using systems and methods for determining parturition onset in animals.

5.1 Definitions

The terms used in this specification generally have their ordinary meanings in the art, within the context of this disclosure and in the specific context where each term is used. Certain terms are discussed below, or elsewhere in the specification, to provide additional guidance in describing the compositions and methods of the disclosure and how to make and use them.

As used herein, the words "a" or "an," when used in conjunction with the term "comprising" in the claims and/or the specification, can mean "one," but they are also consistent with the meaning of "one or more," "at least one," and/or "one or more than one." Furthermore, the terms "having," "including," "containing" and "comprising" are interchangeable, and one of skill in the art will recognize that these terms are open ended terms.

The terms "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to systems or processes, the term can mean within an order of magnitude, preferably within 5-fold, and more preferably within 2-fold, of a value.

The term "heat" as used herein refers to a stage within a female animal's reproductive cycle during which the animal is receptive to mating.

The term "parturition" as used herein refers to the act of giving birth to offspring or childbirth.

The term "whelping" as used herein refers to the act of a dog giving birth or delivering a puppy or puppies.

The term "puppy" as used herein refers to a young dog less than about 2 years old, as measured from birth. More specifically, "puppy" refers to a young dog as measured from birth to about 6-18 months after birth, depending on the animal's adult size.

The term "dam" as used herein refers to a female parent of an animal.

The term "litter" as used herein refers to offspring at one birth of an animal.

The term "canine" as used herein refers to a dog or of or relating to dogs or to the biological family Canidae. For example, the term "canine" as used herein can refer to domestic dogs.

The terms "sequential" or "sequentially" as used herein means that information is input in a successive manner such that a first portion of information is input at a first time, a second portion of information is input at a second time subsequent to the first time, and so on. The time between sequential inputs can be, for example, one or several days, weeks, months, or the like.

The term "user" as used herein includes, for example, a person or entity that owns a user computer, such as a computing device or a wireless device; a person or entity that operates or utilizes a user computer; or a person or entity that is otherwise associated with a user computer. It is contemplated that the term "user" is not intended to be limiting and can include various examples beyond those described.

The term "reference database" as used herein means a database that includes a set of parturition onset reference information, charts, data points, graphs, media, code, and/or information for animals of specific type, among other measurable factors. The "reference database" can also include one or more predetermined thresholds of animal specific biomarkers.

The term "image" as used herein includes, for example, messages, photos, videos, blogs, advertisements, notifications, and various other types of media which can be visually consumed by a user. It is contemplated that the term "image" is not intended to be limiting and can include various examples beyond those described.

5.2 Systems and Methods for Determining Parturition Onset in Animals

In certain non-limiting embodiments, systems and methods for determining parturition onset in animals are provided. In certain non-limiting embodiments, the system can be a computing system that can include a parturition onset determination application server that can send and receive data to and from a user computer.

The present disclosure further relates to a software application platform which provides a user such as a breeder and/or veterinarian with the ability to receive information relating to an animal's estimated parturition onset as displayed on a customized graphical user interface of a user computer based on one or more data inputs relating to a specific animal. Specifically, a user can be prompted to populate one or more data fields in the customized graphical user interface of the user computer to input data related to the animal. For example, the user can enter an input related to animal specific biomarker, such as body temperature or progesterone levels. The user input can then be encoded and transmitted as data from the user computer to a server. Once the data is received, the server can proceed to decode and process the data. Based on the decoded data, which can include the user inputted one or more animal specific biomarkers, the server can determine at least one of the estimated timing of parturition.

Based on the determined estimated timing of parturition, the server can transmit data to the user computer. For example, the transmitted data can include the determined estimated timing of parturition. The transmitted data can also include customized recommendations and/or intervention steps for the specific animal relating to the animal's estimated timing of parturition. In other examples any additional data can be transmitted based on an analysis of the inputted animal specific biomarkers at the server.

In some non-limiting embodiments, the analysis can be performed by comparing the inputted animal specific biomarkers with a reference database. The reference database can include predetermined thresholds of animal specific biomarkers. Based on the comparison between the inputted animal specific biomarkers and the predetermined thresholds, the server can estimate the timing of parturition, customized recommendations, and/or any intervention steps. In certain non-limiting embodiments, the customized recommendations and/or intervention steps can be compared to previously inputted data. For example, the previously inputted data can be stored within the server, or in a separate storage device to which the server has access. The analysis performed by the server can be based at least on the previously inputted data.

In other non-limiting embodiments, the software application operating on the user computer can allow for wide customization of the inputted animal specific biomarkers, information, data, and/or any other input relating to a variety of animals. The software application operating on the user computer can also allow for the displaying of information, data, recommendations, intervention steps, and/or any other outputs determined by the server. The any other output can be directed to the monitoring and/or evaluation of the animal in relation to the estimated parturition onset of the animal as determined by the server.

FIG. 1 illustrates a computing system 100 configured for determining an animal parturition onset. As shown, the computing system 100 can include a plurality of web servers 108, a parturition onset determination application server 112, and a plurality of user computers 102, for example, mobile/wireless devices (only two of which are shown for clarity). Each of user computers 102 can be connected to a communications network 106 (for example, the Internet). The web servers 108 can communicate with the database 114, for example, via a local connection (for example, a Storage Area Network (SAN) or Network Attached Storage (NAS)) over the Internet (for example, a cloud based storage service). The web servers 108 can be configured to either directly access data included in the database 114 or to interface with a database manager that can be configured to manage data included with the database 114. An account 116 can be a data object that can store data associated with a user, such as the user's email address, password, contact information, billing information, animal information, and the like.

Each user computer 102 can include conventional components of a computing device, for example, a processor, system memory, a hard disk drive, a battery, input devices such as a mouse and a keyboard, and/or output devices such as a monitor or graphical user interface, and/or a combination input/output device such as a touchscreen which not only received input but also displays output. Each web server 108 and the parturition onset determination application server 112 can include a processor, a transceiver, and a system memory (not shown), and can be configured to manage content stored in database 114 using, for example, relational database software, a key value system, and/or a file system. The web servers 108 can be programmed to communicate with one another, user computers 102, and the parturition determination application server 112 using a network protocol such as, for example, the TCP/IP protocol. The parturition determination application server 112 can communicate directly with the user computers 102 through the communications network 106. The user computers 102 can be programmed to execute software 104, such as web browser programs and other software application, and access web pages and/or application managed by web servers 108, for example, by specifying a uniform resource locator (URL) that directs to web servers 108.

In the non-limiting embodiments described below, users can respectively operate the user computers 102 that can be connected to the web servers 108 over the communications network 106. Web pages can be displayed to a user via the user computers 102. The web pages can be transmitted from the web servers 108 to the user's computer 102 and can be processed by the web browser program stored in that user's computer 102 for display through a display device and/or a graphical user interface in communication with the user's computer 102.

In one example, information, data, and/or images displayed on the user's computer 102 can relate to parturition onset information via a graph, chart, text, or date. In some embodiments, user computer 102 can access the information, data, and/or images to be displayed on user computer 102 via an online database. The user's computer 102 can send data to parturition onset determination application server 112 via communications network 106 which, in turn, can receive data or information related to parturition onset from the web servers 108 connected to the database 114 and/or from parturition onset determination application server 112. The information, data, and/or images to be displayed through a graphical user interface of user computer 102. In an embodiment in which the information and/or data related to the parturition onset determination is stored in web servers 108 and/or database 114, the online information and/or images, and/or the parturition onset determination application can be managed with a username and password combination, or other similar restricted access/verification required access method, which allow the user to "log in" and access the information.

It is noted that the user's computer 102 can be a personal computer, laptop, mobile computing device, smart phone, video game console, home digital media player, network-connected television, set top box, and/or other computing devices having components suitable for communicating with the communications network 106. The user's computer 102 can also execute other software applications configured to send and/or receive parturition onset information from the parturition onset determination application server 112, such as, but not limited to, text and/or image display software, and/or media players, among others.

Figure 2:
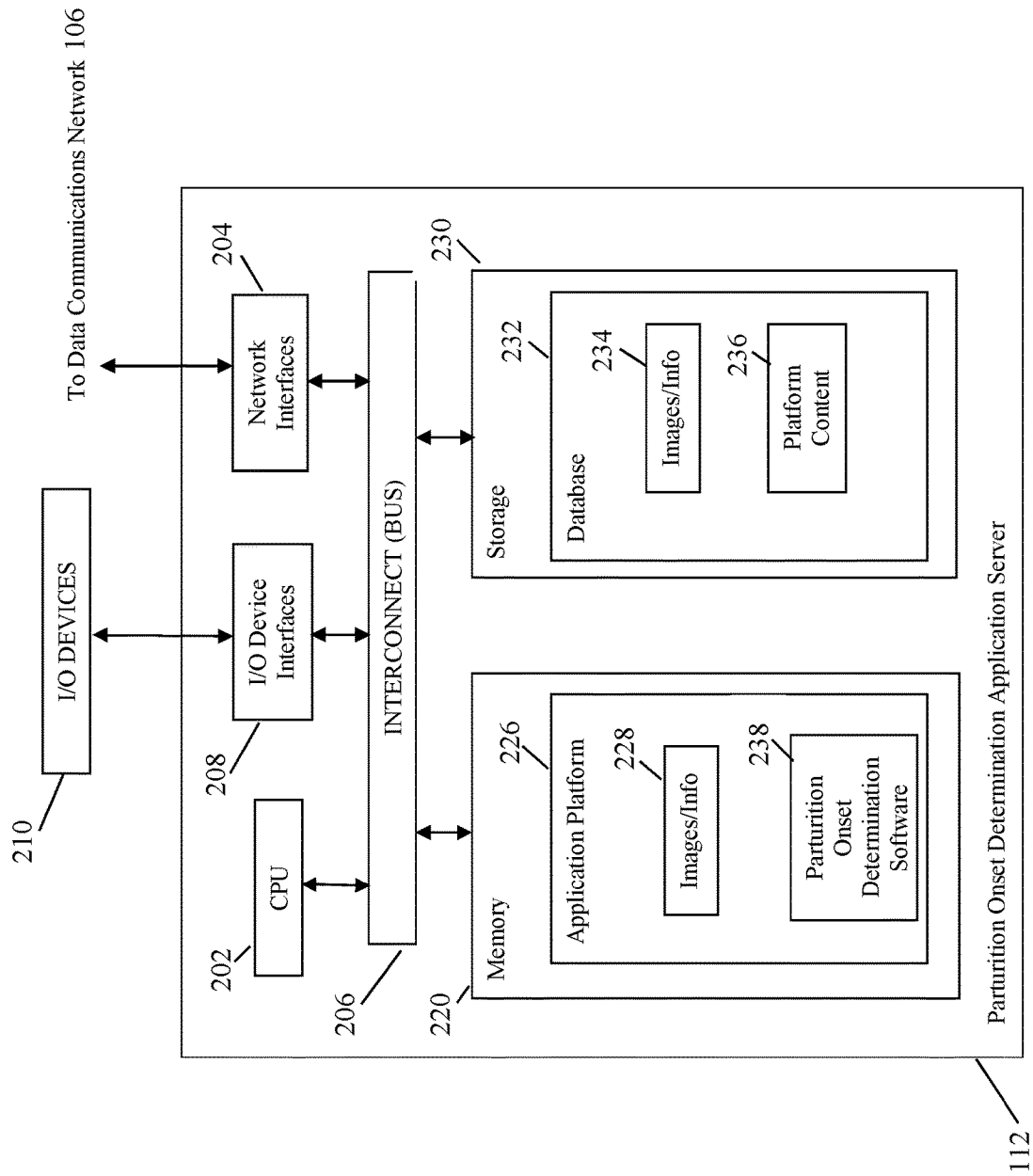
FIG. 2 illustrates a detailed view of a server of FIG. 1 in accordance with certain non-limiting embodiments.

FIG. 2 illustrates a detailed view of a non-limiting embodiment of the parturition onset determination application server 112 of FIG. 1. The parturition onset determination application server 112 can include, without limitation, a central processing unit (CPU) 202, a network interface 204, memory 220, and storage 230 communicating via an interconnect 206. The parturition onset determination application server 112 can also include I/O device interfaces 208 connecting I/O devices 210 (for example, keyboard, video, mouse, audio, touchscreen, etc.). The parturition onset determination application server 112 can further include the network interface 204 configured to transmit data via communications network 106 to user computer 102.

The CPU 202 can retrieve and execute programming instructions stored in the memory 220 and generally can control and coordinate operations of other system components. Similarly, the CPU 202 can store and retrieve application data residing in the memory 220. The CPU 202 can be included to be representative of a single CPU, multiple CPUs, a single CPU having multiple processing cores, and the like. The interconnect 206 can be used to transmit programming instructions and application data between the CPU 202, I/O device interfaces 208, storage 230, network interfaces 204, and memory 220. CPU 202 can be used to process messages received from user computer 102. Based on the processed messages, CPU 202 can be used to determine, for example, an estimated parturition timing, customized recommendations, and/or intervention steps.

The memory 220 can be generally included to be representative of a random access memory (RAM) and, in operation, can store software application and data for use by the CPU 202. Although shown as a single unit, the storage 230 can be a combination of fixed and/or removable storage devices, such as fixed disk drives, floppy disk drives, hard disk drives, flash memory storage drives, tape drives, removable memory cards, CD-ROM, DVD-ROM, Blu-Ray, HD-DVD, optical storage, network attached storage (NAS), cloud storage, a storage area-network (SAN) configured to store non-volatile data, and the like. The reference database can be included within memory 220 and/or storage 230 as database 234.

The memory 220 can store instructions and logic for executing an application platform 226 which can include images 228 and/or parturition onset determination software 238. Parturition onset determination software 238 can be used by CPU 202 to process the data received by partition onset determination application server 112. The storage 230 can store images and/or information 234 and other user generated media and can include a database 232 which can be configured to store images and/or information 234 associated with the application platform content 236. The database 232 can also store application content relating to data associated with user generated media or images and other application features for providing a user with an application platform that can use evidenced-based parturition onset timelines for animals, derived from biomarkers such as body temperature and progesterone levels, among others, to create parturition onset standards applicable to the animals, and to determine parturition onset and recommend intervention. The database 232 can be any type of storage device.

Network computers are another type of computer system that can be used in conjunction with the disclosures provided herein. Network computers do not usually include a hard disk or other mass storage, and the executable programs can be loaded from a network connection into the memory 220 for execution by the CPU 202. A web TV system is also considered to be a computer system, but it may lack some of the features shown in FIG. 2, such as certain input or output devices. A typical computer system will usually include at least a processor, memory, and an interconnect coupling the memory to the processor.

Figure 3:
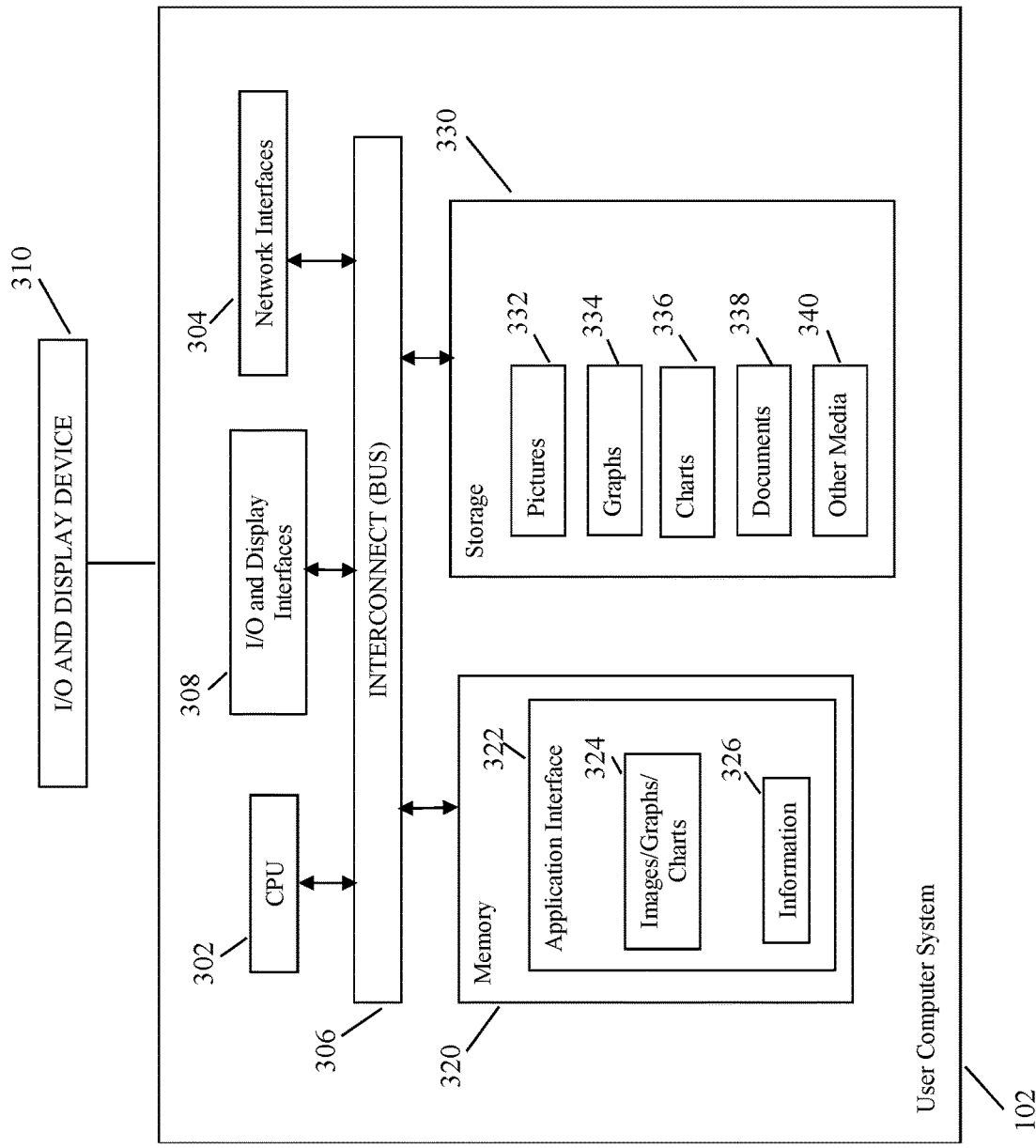
FIG. 3 illustrates a user computer in accordance with certain non-limiting embodiments.

FIG. 3 illustrates a user's computer 102 which can be used to communicate with parturition onset determination application server 112 and display images and/or information associated with the application platform 226. The user's computer 102 can include, without limitation, a central processing unit (CPU) 302, a network interface 304, an interconnect 306, a memory 320, and storage 330. The user's computer 102 can also include an I/O device interface 308 connecting I/O devices 310 (for example, keyboard, display, touchscreen, and mouse devices) to the user's computer 102. A user can be prompted to input data information related the animal into one or more data fields in the customized graphical user interface of user computer 102. For example, the user may enter an input related to animal specific biomarkers, such as body temperature or progesterone levels.

Like CPU 202, CPU 302 can be included to be representative of a single CPU, multiple CPUs, a single CPU having multiple processing cores, etc., and the memory 320 can be generally included to be representative of a random access memory (RAM). CPU 302 can process the information inputted by the user. The interconnect 306 can be used to transmit programming instructions application data between the CPU 302, I/O device interfaces 308, storage 330, network interface 304, and memory 320. The network interface 304 can be configured to transmit data via the communications network 106, for example, to stream or provide content from the parturition onset determination application server 112. Storage 330, such as a hard disk drive or solid-state storage drive (SSD), can store non-volatile data. The storage 330 can contain pictures 332, graphs 334, charts 336, documents 338, and other media 340. Illustratively, the memory 320 can include an application interface 322, which itself can display images 324, such as graphs or charts among others, and/or information 326. The application interface 322 can provide one or more software applications which can allow the user to access media items and other content hosted by the parturition onset determination application server 112.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "analyzing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present example also relates to an apparatus for performing the operations herein. This apparatus can be specially constructed for the required purposes, or it can comprise a general purpose computer selectively activated or reconfigured by a computer program stored in the computer. Such a computer program can be stored in a computer readable storage medium, such as, but is not limited to, read-only memories (ROMs), random access memories (RAMs), EPROMs, EEPROMs, flash memory, magnetic or optical cards, any type of disk including floppy disks, optical disks, CD-ROMs, and magnetic-optical disks, or any type of media suitable for storing electronic instructions, and each coupled to a computer system interconnect.

The algorithms and displays presented herein are not inherently related to any particular computer or other apparatus. Various general purpose systems can be used with programs in accordance with the teachings herein, or it can prove convenient to construct a more specialized apparatus to perform the required method operations. The structure for a variety of these systems will appear from the description above. In addition, the present examples are not described with reference to any particular programming language, and various examples can thus be implemented using a variety of programming languages.

As described in greater detail herein, embodiments of the disclosure provide a software application through which a user can receive customized information relating to an animal's estimated parturition onset as displayed on a graphical user interface based on data input relating to a specific animal. Furthermore, the user can customize, via a selection of at least one biomarker, the information received and displayed on a graphical user interface from which the software application can apply and display relevant parturition onset determination information and/or an intervention recommendation.

Figure 4:
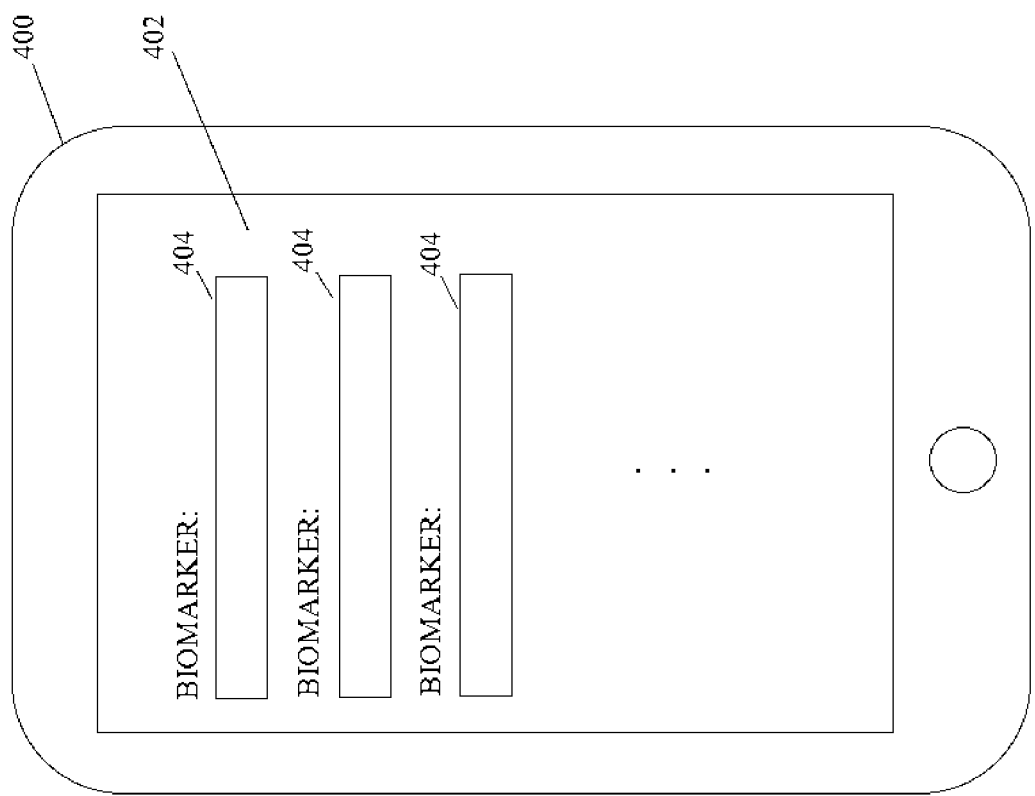
FIG. 4 illustrates a diagram of a graphical user interface in accordance with certain non-limiting embodiments.

FIG. 4 is a diagram illustrating a graphical user interface of a user computer. In particular, FIG. 4 illustrates a parturition onset determination mobile or web application display on a user computer 400 according to certain non-limiting embodiments described herein. The mobile or web application illustrated in FIG. 4 can be accessible via a web browser application (not illustrated) and can include a plurality of web-based user interface elements, for example, a header, a footer, a body, borders, links, text blocks, graphics, images, media, charts, graphs, and the like, which can be arranged to present digital information, customized recommendations, and/or images on a web page within the web browser application. For example, the interface shown in user computer 400 can include a graphical user interface or display 402, that can be configured to receive user input, and/or display information, recommendation(s), and/or images contained within the web page based on the user input.

In certain non-limiting embodiments, a web-based application that utilizes a global portal can be used. For example, as shown in FIG. 1, the global portal can be accessed by a user via a user computer 102 by communicating with network 106. Network 106 can then connect user computer 102 to the global portal. To enter the global portal, a user can input a username and/or password. Once accessed, the user can input one or more biomarkers into the global portal. The global portal can then use the one or more biomarkers to determine an estimated timing of parturition onset and/or provide a customized recommendation.

Referring to FIG. 4, a user can input information pertaining to one or more biomarkers related to an animal into data fields 404. For example, the user can input the body temperature or progesterone concentrations of an animal. The inputted information can then be encoded and transmitted to a sever, such as parturition onset determination application server 112, which can receive the one or more inputted biomarkers from user computer 400. While FIG. 4 illustrates three separate biomarker input fields, other embodiments may include one or more input fields. After the one or more biomarkers are transmitted to the server, the user computer can receive at least one of a customized recommendation and/or an estimated timing of parturition onset related to the animal. User computer 400 can then display the customized recommendation and/or the estimated timing of parturition on graphical user interface 402, not shown in FIG. 4.

In certain embodiments, the one or more biomarkers can include a biomarker measured prior to, during, or after pregnancy of a specific animal. In certain embodiments, the one or more biomarkers can relate to several peri-estrous predictors, predictors during gestation, and predictors near parturition for indicating parturition onset as discussed in further detail below. For example, and not by way of limitation, the one or more biomarkers can include the estimated day of ovulation, estimated beginning of cytological diestrus, measurements determined by ultrasound examination, body temperature, hormone levels, measurements determined by radiographic examination, and/or other health related biomarkers. Peri-estrous predictors can include, for example, the estimated day of ovulation and the beginning of cytological diestrus. Predictors during gestation can include measurements determined by ultrasound examination (e.g., diameter of the inner chorionic cavity, biparietal diameter, and size of the diencephalo-telencephalic vesicle). Predictors near parturition can include measurements determined by ultrasound examination (e.g., fetal gastro-intestinal motility and fetal heart beats), progesterone levels, and body temperature (e.g., rectal or vaginal temperature). For example, and not by way of limitation, the following disclosure will be provided with reference to parturition onset in dogs (i.e., whelping). A person skilled in the art will appreciate that various types of biomarkers are suitable for use with the present disclosure.

In certain non-limiting embodiments, the one or more biomarkers can include the estimated day of ovulation inputted by the user. In other non-limiting embodiments, a server can determine the estimated day of ovulation based on one or more biomarkers, and can transmit the estimate to the user computer. The user computer can then display the estimated day of ovulation. The estimated day of ovulation can be measured by various means, for example and not by way of limitation, by vaginal cytology, ultrasound examination, vaginoscopy, vaginal resistivity testing, luteinizing hormone (LH) concentration (e.g., in the blood), or progesterone concentration (e.g., in the blood), or combinations thereof. For example, the estimated day of ovulation can be measured by a combination of progesterone concentration (e.g., in the blood) and ultrasound examination. The progesterone concentration can be measured, for example, by an enzyme-linked immunosorbent assay (ELISA) kit. The estimated day of ovulation can be used to determine "Day 0" for purposes of measuring a date of estimated parturition.

In certain non-limiting embodiments, the one or more biomarkers can include the estimated beginning of cytological diestrus. In other non-limiting embodiments, a server can determine the estimated beginning of cytological diestrus based on one or more biomarkers, and can transmit the estimate to the user computer. The user computer can then display the estimated beginning of cytological diestrus. The cytological diestrus stage can be measured by various means, for example and not by way of limitation, by vaginal cytology. In female dogs, for example, from the beginning of heat, the first day of cytological diestrus can be defined by a drop in the percentage of vaginal epithelial superficial cells and an increase in intermediate and parabasal cells. For example, and not by way of limitation, the percentage of vaginal epithelial superficial cells can drop at least about 20%, and the percentage of intermediate and parabasal cells can increase at least about 10% in order to indicate the beginning of cytological diestrus.

In certain non-limiting embodiments, the one or more biomarkers can be determined by ultrasound examination. For example and not by way of limitation, the one or more biomarkers can include the diameter of the inner chorionic cavity, the biparietal diameter, or the size of the diencephalo-telencephalic vesicle as determined by ultrasound examination. For example, the inner chorionic cavity can be measured by ultrasound examination at approximately 4 weeks of gestation. Additionally, for example, the biparietal diameter can be measured by ultrasound examination at approximately 5 weeks of gestation. Fetal gastro-intestinal motility can also be measured by ultrasound examination. In the final days of gestation, the gastrointestinal tract of the canine fetus can be matured and therefore can be fully functional. Several aspects of the maturity of the gastrointestinal tract can therefore be observed and measured by ultrasound examination (e.g., identification of a complete intestinal wall; visual distinction between the mucosal surface and the intestinal wall; delineation of intestinal wall layers; segmental dilatation of the bowel by intraluminal mucous and fluid content; and peristalses in all segments of the bowel). Further, fetal heart beats can also be measured by ultrasound examination. For example, oscillations in fetal heart rate can be measured. Fetal biometry can also be measured by ultrasound examination including, for example, fetal kidney shape.

A person skilled in the art will appreciate a wide variety of biomarkers can be determined by ultrasound examination and suitable for use with the present disclosure. In certain non-limiting embodiments, a user can input the one or more biomarkers based on the results of the ultrasound examination. In other non-limiting embodiments, however, the ultrasound machine can communicate the resulting one or more biomarkers directly with the server, without requiring user input. The server can then use the one or more biomarkers received from the ultrasound machine to determine the estimated timing of parturition onset and/or the customized recommendation based on the estimated timing of the parturition onset. The server can then transmit the estimated timing of parturition onset and/or the customized recommendation to the user computer, which can display the estimated timing or the customized recommendation to the user.

In certain non-limiting embodiments, the one or more biomarkers can include body temperature. Body temperature can be measured, for example and not by way of limitation, by measuring vaginal or rectal temperature. Body temperature can be measured by various methods. For example, body temperature can be measured through use of a thermometer, for example, a digital thermometer. The thermometer can be inserted into the animal. For example, the thermometer can be inserted into the rectum of the animal for a certain amount of time, for example, for approximately 1 minute or for greater than approximately 1 minute. Body temperature can also be measured via a microchip implanted in the animal. The microchip can be a thermo microchip. The thermo microchip can be implanted in the animal, for example, via a syringe. The thermo microchip can use radio frequency technology among others to determine the body temperature of the animal. In certain other non-limiting embodiments, the microchip can detect one or more biomarkers and transmit the one or more biomarkers directly to parturition onset determination application server 112, without any input from the user.

In certain non-limiting embodiments, the one or more biomarkers can include hormone levels. For example, the one or more biomarker can include progesterone levels. Progesterone levels can be measured by, for example, a progesterone assay (e.g., as performed by an enzyme-linked immunosorbent assay (ELISA) kit)). A person skilled in the art will appreciate a wide variety of hormone level measurements can be suitable for use with the present disclosure.

In certain non-limiting embodiments, a series of biomarkers prior to and over the duration of pregnancy of the animal can be inputted into the user computer and/or the parturition onset determination application operating on the user computer. Ongoing measurements of certain biomarkers can be useful, for example, in allowing a breeder or a veterinarian to estimate parturition onset and monitor the pregnancy of the animal. For example, the series of biomarkers can be inputted into the parturition onset determination application as measured and described in more detail below. In other words, one or more first biomarkers can include the first biomarker being measured at different times. For example, in certain embodiments one or more first biomarkers can include the first biomarker measured at least one time, at least two times, or at least three times for a predetermined time period, which can be repeated as desired. When the server determines that the estimated timing of parturition onset, the server can account for the change or variation in the one or more first biomarkers observed over time.

By way of example and not limitation, a series of one or more biomarkers can be inputted into the parturition onset determination application operating on user computer 102. In one non-limiting example, the parturition onset (i.e., whelping) in dogs can be determined as follows. The day of ovulation can be measured, for example, by progesterone assay. The dog can then be mated post ovulation and the date of insemination can be defined as "Day 0". The user can input the date of insemination into a data field on the user computer 102, which can forward the date of insemination to the parturition onset determination server 112. At approximately "Day 53" of pregnancy until whelping, body temperature can be measured at least two times per day. For example, in certain embodiments, body temperature can be measured at least three times per day. Body temperature can be measured, for example, by measuring rectal temperature. The measured body temperature can then be transmitted to the parturition onset determination server 112. Based on the received body temperature measurements and/or the date of insemination, the server can determine an estimated whelping onset within the following 24 hours. For example, a drop of body temperature of about 0.5° C. can indicate an onset of whelping within the following 24 hours.

By way of example and not limitation, a series of biomarkers can be transmitted to the parturition onset determination application server 112 for determining the parturition onset (i.e., whelping) in dogs as follows. The day of ovulation can be determined, for example, by a progesterone assay and ultrasound examination. The dog can then be mated post ovulation and the date of insemination can be defined as "Day 0". The beginning of diestrus can be determined, for example, through vaginal cytology. The day of ovulation, date of insemination, and/or results of vaginal cytology can be transmitted to parturition onset determination application server 112. At approximately "Day 35" of pregnancy, a fetal biometry by ultrasound examination can be performed. At approximately "Day 53" of pregnancy until whelping, body temperature can be measured at least two times per day. For example, body temperature can be measured three times per day. Body temperature can be measured, for example, by measuring rectal temperature. Rectal temperature can be measured, for example, by a thermo microchip from approximately "Day 53" of pregnancy until whelping. Rectal temperature can alternatively be measured by a thermometer. Progesterone assays can be performed in order to determine progesterone levels every day from approximately "Day 53" of pregnancy until whelping. The measured temperatures and/or the results of the progesterone assays can be transmitted form the user or a microchip to parturition onset determination application server 112. Ultrasound examination can also be performed prior to whelping in to observe fetal intestinal motility and fetal heart rate. Whelping can occur, for example, at approximately "Day 63" of pregnancy.

The parturition onset determination application server 112 can analyze the one or more biomarkers inputted into data fields 404. A reference database can be subsequently utilized to analyze the one or more biomarker input(s). The reference databased can be located within the parturition onset determination application server 112 or in a separate location that can be accessed by server 112. In certain embodiments, the reference database can include parturition reference information for various animals/breeds/species, etc. The reference database can utilize evidence-based parturition onset timing information, derived from biomarkers such as ovulation date, body temperature, and progesterone assay results, among others, to create patterns applicable to parturition onset in certain animals. In certain embodiments, any other parameter or biomarker can be transmitted to server 112. For example, parameters and biomarkers occurring after birth can be inputted into user computer 102 and transmitted to the parturition onset determination application server 112. For example, and not by way of limitation, in relation to dogs, the age of the dam at whelping, the season of whelping, the litter size, the time of day of whelping, can also be inputted to provide further information for the reference database.

In certain embodiments, the parturition onset determination application server 112 can receive information directly from a microchip implanted in the animal. Thus, in certain embodiments, user input is not required. In certain embodiments, the microchip can be a thermo microchip for measuring body temperature. For example, a dog can be implanted with a thermo microchip. The thermo microchip can measure body temperature and relay the information such as body temperature measurements to a device of a user (e.g., a smart phone of a breeder). Upon a drop in body temperature, which can indicate impending parturition, upon receipt of the information from the thermo microchip to the device of the user, the device can provide the user with an alert. From the alert, the user can then monitor the dog nearing parturition as needed.

After analyzing the one or more biomarkers, the parturition onset determination application server 112 can select relevant parturition onset information based on the one or more biomarkers, and can transmit at least one of the customized recommendation and the estimated timing of parturition onset to a user computer. The user computer, such as user computer 400 or user computer 102, can then display the received customized recommendation and the estimated timing of parturition onset. In other non-limiting embodiments any other information relating to animal parturition can be displayed. For example, the user computer can display the animal's predicted parturition onset date. In certain embodiments, the user computer can display include charts, graphs, graphics, messages, text, icons, or the like. In certain embodiments, the parturition onset determination application server 112 can compare the one or more biometrics and previously utilized biometric inputs of the particular animal to the reference database or to each other. Corresponding intervention recommendations can be based on the estimated timing of parturition onset and/or based on the comparison to previously utilized biometrics, as described below.

In certain non-limiting embodiments, an intervention or action can be recommended based on any one of the biomarkers inputted into data fields 404 of the user computer.

By way of example and not limitation, an intervention or action can be recommended by the output based on any one of the one or more biomarker inputs for determination of parturition onset such as whelping onset in dogs as follows. Initially, the user can input a day of estimated ovulation. The day of estimated ovulation can be determined, for example, by hormone levels such as progesterone levels during heats. The estimated day of ovulation can be used as "Day 0" for parturition onset determination. If the day of ovulation is unknown, fetal biometry can be recommended to provide information relating to parturition onset determination. Approximately 56 days after ovulation, if there is a drop in body temperature (e.g., about 0.5° C. in approx. 12 hours to approx. 24 hours), assessment of hormone levels such as progesterone levels can be recommended. If there is no drop of body temperature, continuation of body temperature monitoring can be recommended. If, for example, hormone levels such as progesterone levels are at a predetermined threshold level (e.g., <about 2.7 ng/mL), parturition can be estimated to onset within the following approximately 24 to 48 hours. If, for example, hormone levels such as progesterone levels are not at the predetermined threshold level, evaluation of progesterone levels every 12 hours can be recommended. Further, if progesterone levels are not at the predetermined threshold level, the control of body temperature can be recommended. A person skilled in the art will appreciate a wide variety of biomarkers are suitable for use with the present disclosure and can be used as biomarker inputs which can determine the output recommendation of an intervention or action based on the one or more biomarker inputs.

In certain embodiments, the parturition onset determination application server 112 can store and/or monitor estimated parturition onset determinations for multiple animals and can further be accessed by multiple users via multiple devices. The data of each animal and a corresponding associated profile can be transferrable to and/or accessed by different users through the parturition onset determination application on any device or system interface. A specific animal can be identified by a unique identification tag, code, picture, number, or the like, which a user can input to retrieve the specific animal's profile and/or history.

In certain embodiments, information received by the parturition onset determination application server 112 can be added to the reference database in order to consistently update the reference database in real time. As such, the real time date can be used in clinical or veterinary studies to provide guidance about estimated parturition onset given particular parameters, etc. As such, the use of historical data can preempt the need for future intervention by adjusting and self-updating the system.

Figure 5:
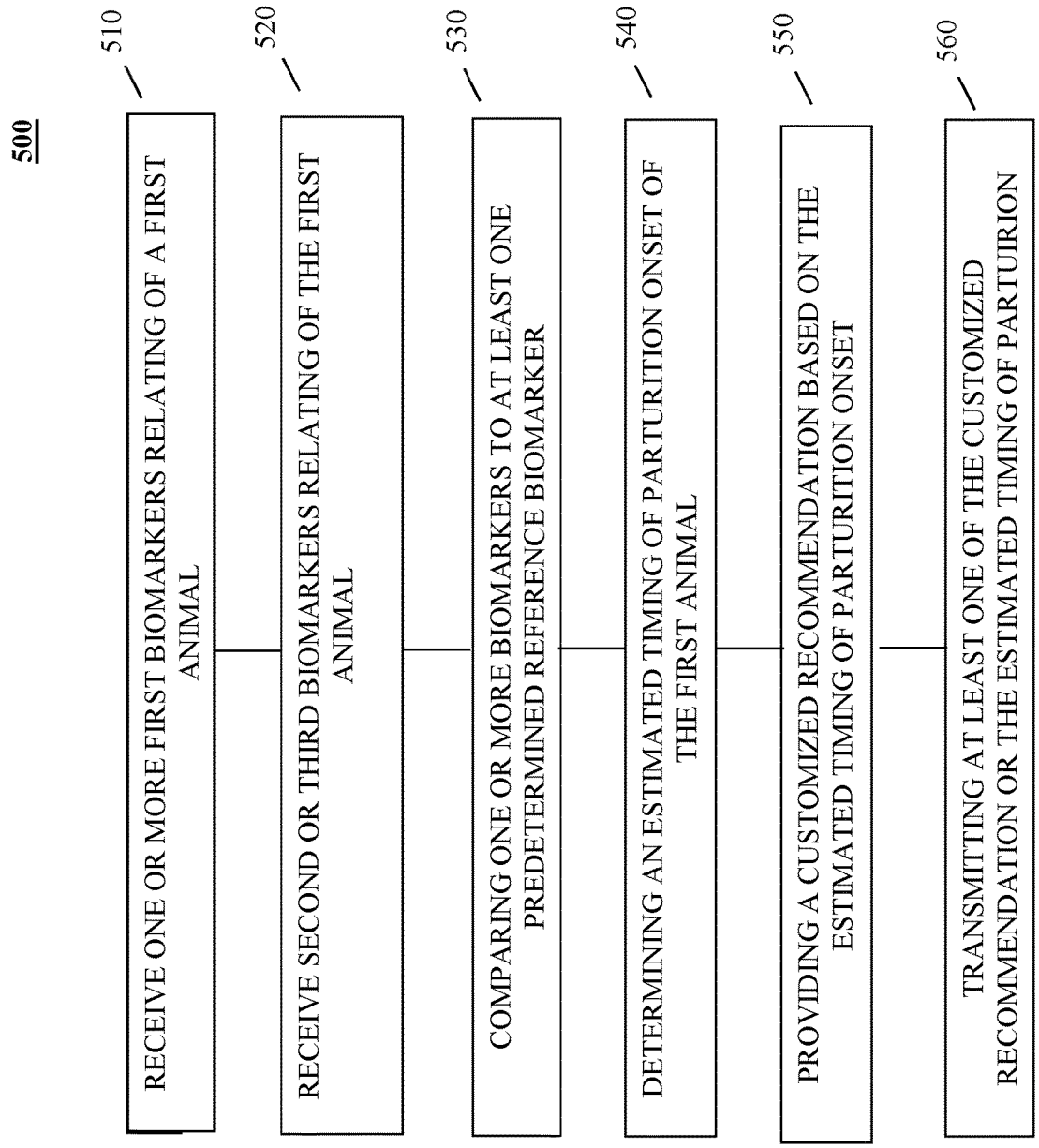
FIG. 5 illustrates a flow diagram of a method in accordance with certain non-limiting embodiments.

FIG. 5 illustrates a flow diagram of a method in accordance with certain non-limiting embodiments. In particular, FIG. 5 illustrates method 500 performed by a server, such as parturition onset determination application server 112, for determining parturition onset in animals according to certain non-limiting embodiments. In one non-limiting example, the server can be accessed using a global portal.

In step 510, the server can receive one or more first biomarkers relating to a first animal. The one or more first biomarkers can be received from the user computer and/or a microchip implanted in the first animal. The one or more first biomarker of the first animal can include, for example, at least one of a body temperature of the first animal or a serum progesterone concentration of the first animal. In step 520, the server can receive at least one of a second or third biomarker. The first, second, and/or third biomarker can be different biomarkers. The one or more biomarker inputs can be any biomarker discussed above.

In step 530, the one or more first biomarkers related to the first animal can be compared, at the server, to at least one predetermined biomarker stored in a reference database. The at least one predetermined reference biomarker can include a threshold value of the one or more first biomarkers. The threshold value can be used as part of the determining or providing in steps 540 and 550. For example, if one or more first biomarkers, such as an animal's temperature, falls below the threshold value in the reference database, the server can determine that the estimated timing of partition can be within a particular timeframe, for example, within 24 hours. In certain non-limiting embodiments, the predetermined reference biomarker can be based on the one or more first biomarkers received by the server for a second animal. The received one or more first biomarkers relating to the first animal can be stored in the reference database. The predetermined reference biomarker can be based on the one or more first biomarkers relating to the first animal stored in the reference database.

In step 540, the server can determine an estimated timing of parturition onset of the first animal. The determining can be based on the one or more first biomarker and/or at least one of the second and/or third biomarkers. In step 550, the server can provide a customized recommendation based on the estimated timing of parturition onset. The customized recommendation can include an intervention step requesting at least one additional biomarker for the first animal. In response, the server can receive at least one additional biomarker for the first animal in response to the intervention step. The estimated timing of parturition can determine the onset of the first animal based on the additional biomarker. In step 560, the server can transmit at least one of the customized recommendation and/or the estimated timing of parturition onset to a user computer.

Figure 6:
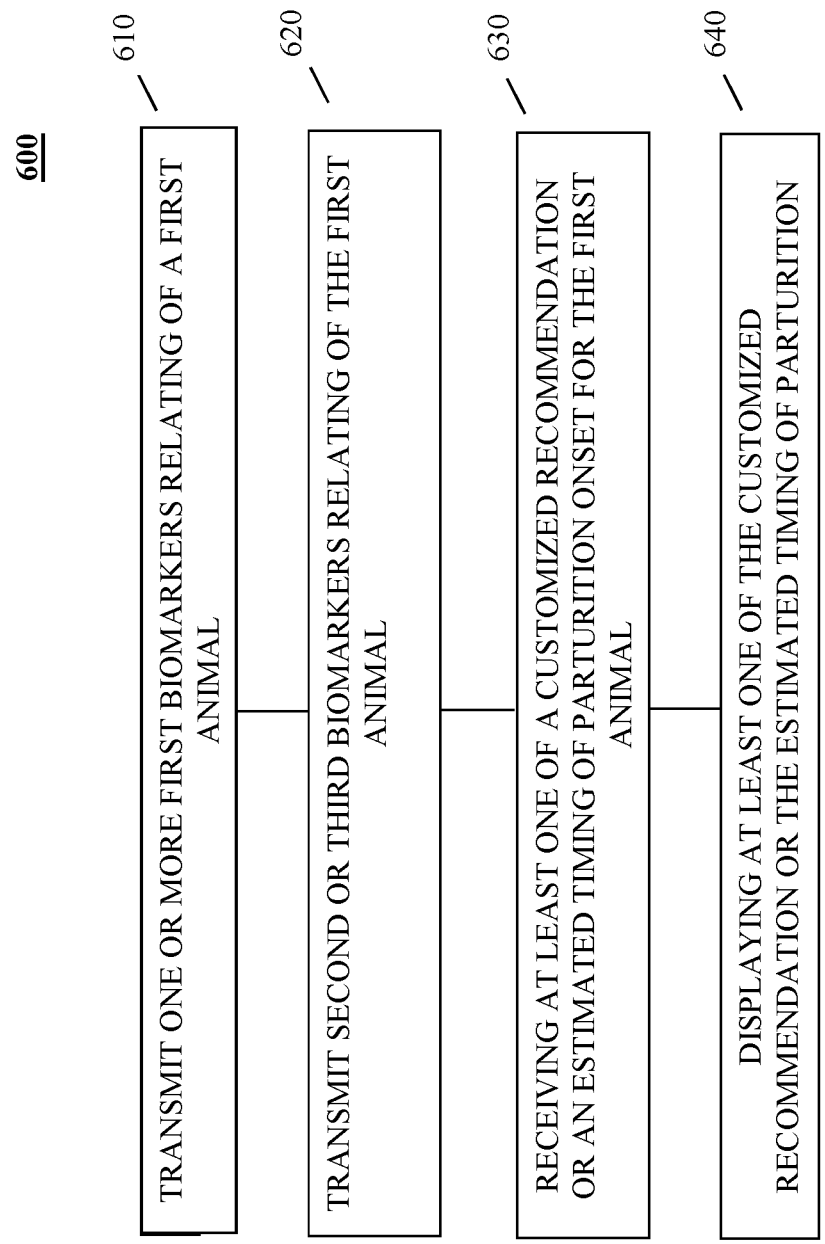
FIG. 6 illustrates a flow diagram of a method in accordance with certain non-limiting embodiments.

FIG. 6 illustrates a flow diagram of a method in accordance with certain non-limiting embodiments. In particular, FIG. 6 illustrates method 600 performed by a user computer, such as user computer 102 or user computer 400. In step 610, the user computer can transmit to a server one or more first biomarkers relating to a first animal. The one or more first biomarkers of the first animal can include, for example, at least one of a body temperature of the first animal or serum progesterone concentration of the first animal. In step 620, the user computer can transmit at least one of a second or third biomarker. The first, second, and/or third biomarkers can be different. In certain non-limiting embodiments, the user can be prompted to enter the one or more first biomarkers relating to the first animal, while in other non-limiting embodiments the one or more first biomarkers can be received from the microchip implanted in the first animal.

In step 630, the user computer can receive at least one a customized recommendation and/or an estimated timing of parturition onset for the first animal. The customized recommendation and/or an estimated timing of parturition onset for the first animal can be based on the transmitted one or more first biomarkers, the second biomarker, and/or the third biomarker, or any combination thereof. In step 640, at least one of the customized recommendation or the estimated timing of parturition onset for the first animal can be displayed on a graphical user interface of the user computer.

In certain non-limiting embodiments, the user can perform an intervention step in response to the displayed customized recommendation and/or the estimated timing of parturition onset for the first animal. For example, the customized recommendation can include an intervention step requesting at least one additional biomarker for the first animal. In response, the user computer can transmit the at least one additional biomarker for the first animal. The user computer can subsequently receive the estimated timing of parturition onset for the first animal based on the additional biomarker.

5.3. Methods of Using Systems and Methods for Determining Parturition Onset in Animals The methods, devices and systems of the present disclosure can be provided in one or more kits for use. The one or more kits can include, for example and not by way of limitation, a digital thermometer, a thermo microchip, an ultrasound machine, an enzyme-linked immunosorbent assay (ELISA) kit (e.g., for progesterone assays), one or more swabs (e.g., vaginal swabs), one or more microscope slides, a staining (e.g., a Harris-Shorr stain), a microscope, or combinations thereof and optionally instructions for use. The kits can also include a web application. The web application can be used, for example, to read and interpret the measured one or more biomarkers of a specific animal (e.g., body temperature evolution). The instructions for use can set forth any of the methods of the present disclosure. Optionally, such kits can further include any of the other systems components described in relation to the present disclosure and any other materials or items relevant to the present disclosure.

In certain non-limiting embodiments, the methods, devices and systems of the present disclosure can be used as a tool by a user, for example, a breeder or a veterinarian. The user can utilize embodiments of the present disclosure, for example, to monitor the pregnancy of an animal and to track estimated timing of parturition. Based on observations therefrom, the user, for example a breeder or a veterinarian, can make recommendations or interventions regarding the animal's pregnancy (e.g., the scheduling and performance of a caesarian section in a prolonged pregnancy).

6. EXAMPLES

The presently disclosed subject matter will be better understood by reference to the following Examples, which are provided as exemplary of the disclosure, and not by way of limitation.

Example 1: Method of Determining Whelping Onset in Dogs Using Rectal Temperature This Example provides a method for determining whelping onset in dogs using one or more biomarkers such as body temperature in accordance with certain embodiments of the present disclosure.

From the same breeding kennel, eighty-six (86) female Labradors and two-hundred seventeen (217) gestations were analyzed. The day of ovulation was measured by a progesterone assay. A blood sample was taken at Day 8 of estrus (i.e., the onset defined as vulvar edema and vulvar discharge). For progesterone concentrations at about 1 ng/mL, a second blood sample was taken in 3 days. For progesterone concentrations at about 4 ng/mL, a second blood sample was taken in 2 days. The day of ovulation was defined at a progesterone concentration at about 8 ng/mL. The female Labradors were inseminated at post-ovulation Day 2 and Day 3. The day of first insemination was defined as Day 0. Rectal temperature was measured three (3) times per day (e.g., at approx. 8 am, approx. 2 pm, and approx. 6 pm) every day from Day 53 until whelping. A digital thermometer (ST8A36CS, Measure Technology, Wuxi City, China, measurement range: 32-42.9° C., precision: ±0.1° C.°) was introduced in the rectum for about 1 minute. The temperature value was than registered on the individual clinical chart. The time of parturition was defined as the expulsion of the first puppy. Linear mixed models (MIXED procedure, R studio software) and year modeled as random effects of the female canines were performed to determine variables affecting body temperature. As fixed effects, this model included: (i) age of the dam at whelping (e.g., in years); (ii) season of whelping (i.e., spring, summer, fall, or winter); (iii) litter size (e.g., total number of puppies born within a single litter); (iv) the time of day (e.g., morning, mid-day, evening), (v) the time before whelping (e.g., hours). Effect Size Index was used for predictive value quantification. Receiver operating characteristic (ROC) curves were drawn and the best cut-off values for high and low probability of parturition were defined based on Youden's index.

In total, approx. 3,879 rectal temperatures were registered. The mean number of rectal temperature measurements per gestation was 18 (min=5; max=32). The mean rectal temperature was approx. 37.6° C.±0.4° C. (mean±SD). Rectal temperatures were influenced by the following factors: (i) age at parturition (p<0.001); (ii) litter size (p<0.001); (iii) time of the day (p<0.001); and (iv) time before whelping. The factor (iv) time before whelping presented a pattern based on the effect size index. Rectal temperature started to decrease approx. 48 hours before whelping (e.g., approx. 37.2° C., approx. 37.6° C. and approx. 37.7° C. for respectively 0-24 h, 24-48 h and 48-168 h before whelping; p<0.05). Models based on only one rectal temperature measurement per day were of lower performances (area under the curve (AUC) between 0.719 and 0.842 depending on the time of the day) than models based on two or three rectal temperature measurements per day (with AUC=0.933 and 0.957 respectively). The most reliable cut off value to discriminate female canines with a relatively high probability of whelping onset in the following 24 h was at approx. 0.4° C. and approx. 0.5° C. for two and three rectal temperature measurements per day, respectively. Predictive negative values (PNV) for these thresholds were relatively high: approx. 99.3% and approx. 99.7%, respectively for two and three rectal temperature measurements per day. Positive predictive values (PPV) were relatively low: approx. 25.2% and approx. 18.4% respectively for two and three rectal temperature measurements per day. Thus, body temperature as determined by rectal temperature measurements was observed to decrease within approx. 48 hours before whelping. Two to three rectal measurements per day provided a more accurate prediction of whelping as compared to a single rectal temperature measurement. Further, the relatively high negative predictive values (NPV) indicated rectal temperature measurements can be indicative of impending parturition and influence decisions whether to monitor the female dog. According to the present Example, if a decrease of body temperature of approx. ≥0.4° C. was not observed in the previous 24 hours, the female canine would not start whelping in the following 24 hours at approx. 99.3% of probability. However, false positive results (a decrease of temperature without whelping in the following 24 hours) were relatively high (e.g., approx. 15%).

The one or more biomarkers provided above can be inputted as data into a parturition onset determination application which can provide recommendations or intervention steps as provided herein.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

While the foregoing is directed to embodiments described herein, other and further embodiments can be devised without departing from the basic scope thereof. For example, aspects of the present disclosure can be implemented in hardware or software or in a combination of hardware and software. One embodiment described herein can be implemented as a program product for use within a computer system. The program(s) of the program product define functions of the embodiments (including methods described herein) and can be contained on a variety of computer-readable storage media. Illustrative computer-readable storage media include, but are not limited to: (i) non-writable storage media (for example, read-only memory devices within a computer such as CD-ROM disks readable by a CD-ROM drive, flash memory, ROM chips or any type of solid-state non-volatile semiconductor memory) on which information is permanently stored; and (ii) writable storage media (for example, floppy disks within a diskette drive or hard-disk drive or any type of solid-state random-access semiconductor memory) on which alterable information is stored. Such computer-readable storage media, when carrying computer-readable instructions that direct the functions of the disclosed embodiments, are embodiments of the present disclosure.

For any patents, patent applications, publications, product descriptions, and protocols are cited throughout this application, the disclosures of all of which are incorporated herein by reference in their entireties for all purposes.

What is claimed is:

1. A method performed by a server for determining timing of parturition onset in non-human animals, comprising:
   receiving, at the server, one or more first biomarkers relating to a first animal;
   comparing, at the server, the one or more first biomarkers relating to the first animal to at least one predetermined reference biomarker stored in a reference database wherein the at least one predetermined reference biomarker comprises a threshold value of the one or more first biomarkers;
   determining, at the server, an estimated timing of parturition onset for the first animal based on the comparison of the one or more first biomarkers;
   providing a customized recommendation based on the estimated timing of parturition onset; and
   transmitting, from the server, at least one of the customized recommendation or the estimated timing of parturition onset to a user computer, wherein the customized recommendation comprises an intervention step requesting at least one additional biomarker for the first animal.

2. The method of claim 1, wherein the at least one predetermined reference biomarker is based on the one or more first biomarkers received by the server for a second animal.

3. The method of claim 1, further comprising:
   storing the received one or more first biomarkers relating to the first animal in the reference database, wherein the at least one predetermined reference biomarker is based on the one or more first biomarkers relating to the first animal stored in the reference database.

4. The method of claim 1, wherein the one or more first biomarkers of the first animal comprises at least one of a body temperature of the first animal or serum progesterone concentration of the first animal.

5. The method of claim 1, further comprising:
   receiving, at the server, the at least one additional biomarker for the first animal in response to the intervention step; and
   determining, at the server, the estimated timing of parturition onset for the first animal based on the additional biomarker.

6. The method of claim 1, wherein the one or more first biomarkers is received from the user computer.

7. The method of claim 1, wherein the one or more first biomarkers is received from a microchip implanted in the first animal.

8. The method of claim 1, wherein the server is accessed using a global portal.

9. A method performed by a user computer, comprising:
   transmitting, from the user computer to a server, one or more first biomarkers relating to a first animal;
   receiving, at the user computer, at least one of a customized recommendation or an estimated timing of parturition onset for the first animal based on the one or more first biomarkers relating to the first animal, wherein the received at least one of a customized recommendation or an estimated timing of parturition onset is based on a comparison of the one or more first biomarkers to a predetermined threshold value of the one or more first biomarkers stored in a reference database within server; and
   displaying at least one of the customized recommendation or the estimated timing of parturition onset for the first animal on a graphic user interface of the user computer, wherein the customized recommendation comprises an intervention step requesting at least one additional biomarker for the first animal.

10. The method of claim 9, further comprising:
    prompting a user to enter the one or more first biomarkers relating to the first animal, wherein the one or more first biomarkers are received from an input by the user; or
    receiving the one or more first biomarkers from a microchip implanted in the first animal.

11. The method of claim 9, wherein a user performs the intervention step in response to at least one of the customized recommendation or the estimated timing of parturition onset for the first animal.

12. The method of claim 9, wherein the one or more first biomarkers of the first animal include at least one of a body temperature of the first animal or serum progesterone concentration of the first animal.

13. The method of claim 9, further comprising:
   transmitting, from the user computer to the server, the at least one additional biomarker for the first animal; and
   receiving, at the user computer, the estimated timing of parturition onset of the first animal based on the additional biomarker.

14. A server for determining timing of parturition onset in non-human animals, comprising:
   a processor; and
   a memory storing instructions that, when executed by the processor, cause the server to:
   receive one or more first biomarkers relating to a first animal;
   compare, at the server, the one or more first biomarkers relating to the first animal to at least one predetermined reference biomarker stored in a reference database, wherein the at least one predetermined reference biomarker comprises a threshold value of the one or more first biomarkers;
   determine an estimated timing of parturition onset for the first animal based on the comparison of the one or more first biomarkers;
   provide a customized recommendation based on the estimated timing of parturition onset; and
   transmit, from the server, at least one of the customized recommendation and the estimated timing of parturition onset to a user computer,
   wherein the customized recommendation comprises an intervention step requesting at least one additional biomarker for the first animal.

* * * * *